Figure 1:
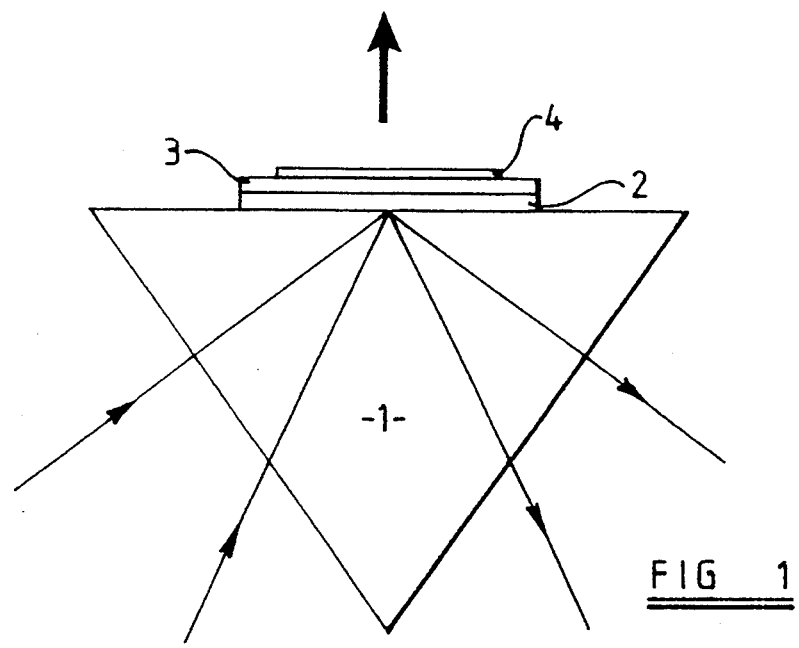

United States Patent [19]
Maule

[11] Patent Number: 5,434,663
[45] Date of Patent: Jul. 18, 1995

[54] ANALYTICAL DEVICE

[75] Inventor: Colin H. Maule, Cambridge, Great Britain

[73] Assignee: Fisons plc, Loughborough, England

[21] Appl. No.: 977,446

[22] PCT Filed: Jul. 12, 1991

[86] PCT No.: PCT/GB91/01161
§ 371 Date: Apr. 15, 1993
§ 102(e) Date: Apr. 15, 1993

[87] PCT Pub. No.: WO92/03720
PCT Pub. Date: Mar. 5, 1992

[51] Int. Cl.⁶ .................. G01J 3/00; G01N 21/55
[52] U.S. Cl. ........................... 356/300; 356/445
[58] Field of Search .............. 356/300, 445, 318

[56] References Cited

U.S. PATENT DOCUMENTS 3,436,159 1/1969 Harrick et al. ............... 356/256
4,558,012 12/1985 Nygren et al. ............... 436/501

FOREIGN PATENT DOCUMENTS 0205236 12/1985 European Pat. Off.
PCT/GB89/01420 6/1990 United Kingdom.

OTHER PUBLICATIONS

*Applied Optics*, vol. 21, No. 12, Jun. 1982, Bosacchi et al., "Resonant Frustrated-Total-Reflection Technique for the Characterization of Thin Films".

Primary Examiner—Vincent P. McGraw
Assistant Examiner—K. P. Hantis
Attorney, Agent, or Firm—Marshall, O'Toole, Gerstein, Murray & Borun

[57] ABSTRACT

A sensor, particularly a resonant optical biosensor based on the principle of frustrated total reflection, includes an optical structure comprising: a) a cavity layer (3) of transparent dielectric material of refractive index $n_3$, b) a dielectric substrate (1) of refractive index $n_1$, and c) interposed between the cavity layer (3) and the substrate (1), a dielectric spacer layer (2) of refractive index $n_2$. The arrangement is such that the optical structure may be illuminated by a beam of incident radiation, internal reflection occurring at the interface between the substrate (1) and the spacer layer (2). The device is characterised in that the cavity layer (3) or the spacer layer (2) absorbs at the wavelength of the incident radiation. The cavity layer (3) or the spacer layer (2) comprises a material which is either absorbing or is doped with an absorbing species, most preferably a fluorophore.

11 Claims, 1 Drawing Sheet

ANALYTICAL DEVICE

This invention relates to sensors, especially those termed biosensors, ie to devices for the analysis of biologically active species such as antigens and antibodies in samples of biological origin. In particular, the invention relates to biosensors based on the principle of resonant attenuated or frustrated total internal reflection.

Many devices for the automatic determination of biochemical analytes in solution have been proposed in recent years. Typically, such devices (biosensors) include a sensitised coating layer which is located in the evanescent region of a resonant field. Detection of the analyte typically utilizes optical techniques such as, for example, surface plasmon resonance (SPR), and is based on changes in the thickness and/or refractive index of the coating layer resulting from interaction of that layer with the analyte. This causes a change, eg in the angular position of the resonance.

Other optical biosensors include a waveguide in which a beam of light is propagated. The optical characteristics of the device are influenced by changes occurring at the surface of the waveguide. One form of optical biosensor is based on frustrated total reflection. The principles of frustrated total reflection (FTR) are well-known; the technique is described, for example, by Bosacchi and Oehrle [Applied Optics (1982), 21, 2167-2173]. An FTR device for use in immunoassay is disclosed in European Patent Application No 2205236A and comprises a cavity layer bounded on one side by the sample under investigation and on the other side by a spacer layer which in turn is mounted on a substrate. The substrate-spacer layer interface is irradiated with monochromatic radiation such that total reflection occurs, the associated evanescent field penetrating through the spacer layer. If the thickness of the spacer layer is correct and the incident parallel wave vector matches one of the resonant mode propagation constants, the total reflection is frustrated and radiation is coupled into the cavity layer. The cavity layer must be composed of material which has a higher refractive index than the spacer layer and which is transparent at the wavelength of the incident radiation.

More recently, FTR biosensors have been described [see, for example, PCT Patent Application WO 90/06503] in which the cavity layer is a thin film of relatively high refractive index material, typically an inorganic oxide.

In devices of this kind, the occurrence of resonance may be detected as a change of phase of the reflected radiation. Measurement of a change of phase is a relatively complex operation and is easily affected by varying birefringence of the substrate or an interposed optical component. This makes the use of inexpensive plastics optics impracticable. It would be desirable if, instead, a device were available which enabled measurements to be made by, for example, detection of the output intensity.

We have now devised a biosensor device based on FTR which enables this to be done.

According to the invention, there is provided a sensor including an optical structure comprising a) a cavity layer of dielectric material of refractive index $n_3$, b) a dielectric substrate of refractive index $n_1$, and c) interposed between the cavity layer and the substrate, a spacer layer of refractive index $n_2$, $n_3$ and $n_1$ both being greater than $n_2$, the cavity layer being of sufficient thickness to support at least one resonant mode, and the arrangement being such that the optical structure may be illuminated by a beam of incident radiation, internal reflection occurring at the interface between the substrate and the spacer layer, characterised in that the cavity layer or the spacer layer absorbs at the wavelength of the incident radiation.

The sensor according to the invention is advantageous primarily in that resonance may be detected as a reduction in the intensity of the reflected radiation. Such a drop in intensity requires a less elaborate detection system than is necessary for the detection of a phase change. Also, relatively inexpensive plastics optical components may be used. This means that simpler instrumentation may be used, with concomitant cost savings.

The cavity layer or spacer layer should absorb sufficiently strongly for a detectable reduction in intensity to be obtained. On the other hand, the absorption should not be so great as to cause significant broadening of the resonance.

Examples of absorbing materials which may be used for the cavity layer and the spacer layer are:

for the spacer layer, a metal, eg silver, or a dielectric material which either is strongly absorbing or which is doped with a strongly absorbing species. An example of the latter case is a magnesium fluoride layer doped with a transition metal fluoride, eg $CuF_2$ or $NiF_2$.

for the cavity layer, a dielectric material which either is strongly absorbing or which is doped with a strongly absorbing species. An example is titanium dioxide or zirconium dioxide doped with a suitable absorbing species, eg CuO.

Where either the cavity layer or the spacer layer is non-absorbing, it may be formed of the above-mentioned dielectric materials without dopants.

Obviously, the absorbing species must be chosen with reference to the wavelength of the incident radiation. Greater flexibility may be possible by the use of organic materials, eg organic dyes.

In a further alternative, the absorbing material may be in the form of an additional thin layer in the sandwich structure of substrate, spacer layer and cavity layer.

In use, the interface between the substrate and the spacer layer is irradiated with light such that internal reflection occurs. In this context, 'light' may include not only visible light but also wavelengths above and below this range, eg in the ultra-violet and infra-red.

Resonant propagation of a guided mode in the cavity layer will occur, for a given wavelength, at a particular angle of incidence of the exciting radiation. Thus, two basic measurement approaches are possible: scanning the angle of incidence at fixed wavelength or scanning the wavelength at a fixed angle of incidence. The former approach, using monochromatic radiation, is preferred since it allows the use of a laser source, simplifying the problem of optical collimation, and avoids dispersion effects, thereby simplifying the analysis of the results.

The angular position of the resonant effect depends on various parameters of the biosensor device, such as the refractive indices and thicknesses of the various layers. In general, it is a pre-requisite that the refractive index $n_3$ of the cavity layer and the refractive index $n_1$ of the substrate should both exceed the refractive index $n_2$ of the spacer layer. Also, since at least one mode must exist in the cavity to achieve resonance, the cavity layer must exceed a certain minimum thickness.

The cavity layer is preferably a thin-film of dielectric material. Suitable materials for the cavity layer include zirconium dioxide, titanium dioxide, aluminium oxide and tantalum oxide.

The cavity layer may be prepared by known techniques, eg vacuum evaporation, sputtering, chemical vapour deposition or in-diffusion.

The dielectric spacer layer must have a lower refractive index than both the cavity layer and the substrate. The layer may, for example, comprise an evaporated or sputtered layer of magnesium fluoride. In this case an infra-red light injection laser may be used as light source. The light from such a source typically has a wavelength around 800 nm. Other suitable materials include lithium fluoride and silicon dioxide. Apart from the evaporation and sputtering techniques mentioned above, the spacer layer may be deposited on the substrate by a sol-gel process, or be formed by chemical reaction with the substrate.

The sol-gel process is particularly preferred where the spacer layer is of silicon dioxide.

The refractive index of the substrate ($n_1$) must be greater than that ($n_2$) of the spacer layer but the thickness of the substrate is generally not critical.

By contrast, the thickness of the cavity layer must be so chosen that resonance occurs within an appropriate range of coupling angles. The spacer layer will typically have a thickness of the order of several hundred nanometers, say from about 200 nm to 2000 nm, more preferably 500 to 1500 nm, eg 1000 nm. The cavity layer typically has a thickness of a few tens of nanometers, say 10 to 200 nm, more preferably 30 to 150 nm, eg 100 nm.

It is particularly preferred that the cavity layer has a thickness of 30 to 150 nm and comprises a material selected from zirconium dioxide, titanium dioxide, tantalum oxide and aluminium oxide, and the spacer layer has a thickness of 500 to 1500 nm and comprises a material selected from magnesium fluoride, lithium fluoride and silicon dioxide, the choice of materials being such that the refractive index of the spacer layer is less than that of the cavity layer.

Preferred materials for the cavity layer and the spacer layer are tantalum oxide and silicon dioxide respectively.

Of course, in the above cases the cavity layer or the spacer layer will contain an absorbing dopant.

Any convenient source of radiation may be used as the source of the incident light but it is preferable to use monochromatic radiation and the most convenient source of such radiation is a laser. The choice of laser will depend inter alia on the materials used for the various layers of which some examples have already been given, and of course on the wavelength at which the cavity layer or spacer layer absorbs.

The scanning of angle may be performed either sequentially or simultaneously ie by varying the angle of incidence of a parallel beam of light or by simultaneously irradiating over a range of angles using a fan-shaped beam of light as described (in connection with SPR) in European Patent Application No 0305109A. In the former case, a single-channel detector may be used which is mechanically scanned over a range of angles; in the latter case, in which a range of angles is irradiated simultaneously, it will generally be necessary to use a multi-channel detector having angular resolution.

At resonance, the incident light is coupled into the cavity layer by FTR, propagates a certain distance along the cavity layer and couples back out (also by FTR). The propagation distance depends on the various device parameters but is typically of the order of 1 or 2 mm.

Light coupled into the cavity layer at resonance may be absorbed by the absorbing cavity layer or spacer layer, resulting in a reduction in the intensity of the reflected light.

In a preferred embodiment of the sensor according to the invention, the cavity layer or spacer layer contains a fluorophore. This enables resonance to be detected as an increase in the intensity of emitted fluorescence.

A wide range of fluorophores may be employed, although obviously the choice of fluorophore will depend on the wavelength of the exciting radiation (and vice versa).

In this case, in a first configuration, the angle of incidence is scanned through a range of angles, and internal reflection takes place. At the appropriate angle of incidence, however, resonance occurs and energy from the incident radiation is coupled into the cavity layer. Propagation of the radiation coupled into this layer results in an increase in the intensity of the emitted fluorescence. The emitted fluorescence may be measured by a detector positioned above the optical structure (though in this case there may be interference due to absorbance, scattering etc in the sample under test), below the optical structure (if the optical structure has an appropriate shape, eg if it is in the form of a Dove prism), or in the reflected beam (provided that the detector is large enough or is scanned in angle with the input beam). In any event, an appropriate filter must be provided to separate the exciting radiation and the emitted fluorescence.

In a second configuration, reliance is placed on the fact that a reasonable fraction of any fluorescence emitted will become trapped within the guiding layer, to be coupled out as a collimated beam at an angle dependent on the device parameters (refractive index and thickness of each layer), the wavelength of the fluorescence and the thickness of the immobilised chemistry. In this case, the fluorescence could be excited by a wedge-shaped beam ie by irradiating at a range of angles simultaneously. The detector may be multi-channel, or a single, scanned device, provided that it is sensitive to the fluorescence wavelength and has sufficient sensitivity.

The cavity layer will generally be sensitised by having biomolecules, eg specific binding partners for the analyte(s) under test, immobilised upon it. The immobilised biochemicals may be covalently bound to the dielectric cavity layer by methods which are well known to those skilled in the art. In general, however, in order to facilitate immobilisation, the dielectric layer will be derivatised or activated. The derivatisation or activation of the surface will be such as to provide coupling sites for the species to be immobilised without appreciably affecting the reactivity or affinity of the immobilised species for the analyte.

For example, the dielectric layer may be reacted with a silane-based coupling compound in a known manner. A suitable such reagent is, for example, a terminal amino-alkyl trimethoxysilane, eg the 3-aminopropyl compound, used at a concentration of about 2% w/v in acetone. Details of immobilisation techniques using this reagent have been described by Weetall [see, for example, US Pat. No. 3,652,761 and "Immobilised Biochemicals and Affinity Chromatography", R B Dunlop (Ed), Plenum Press, New York (1974), pp 191–212], along with a description of other silyl compounds and the methods by which carboxyl, amino and other reactive groups may be covalently bound to various inorganic materials.

After reaction with the amino-silane reagent, the amino terminals immobilised on the cavity layer may in turn be reacted with glutaraldehyde (eg a 2% solution of pH 7), excess reagents removed, and the activated surface with immobilised aldehyde groups then being treated with a solution of the species to be immobilised.

An alternative method for coupling biomolecules to a dielectric surface involves treatment with epoxy-silane reagents, especially glycidyloxypropyltrimethoxysilane, eg at a concentration of about 2% v/v in toluene for about 2 hours at 70° C. as described by Herman et al [J Chromatogr Sci (1981), 19(9), 470–476]. In this method the use of aldehyde reagents is unnecessary, since the epoxysilylated cavity layer can react directly with the species to be immobilised.

Methods of immobilising species to polymeric surfaces are also well-known, and those skilled in the art will recognise the applicability of these methods when the cavity layer is polymeric. For example, the coupling may be in the form of the substitution of an appropriate radical for a hydrogen on any of the polymer's functional groups.

Figure 2:
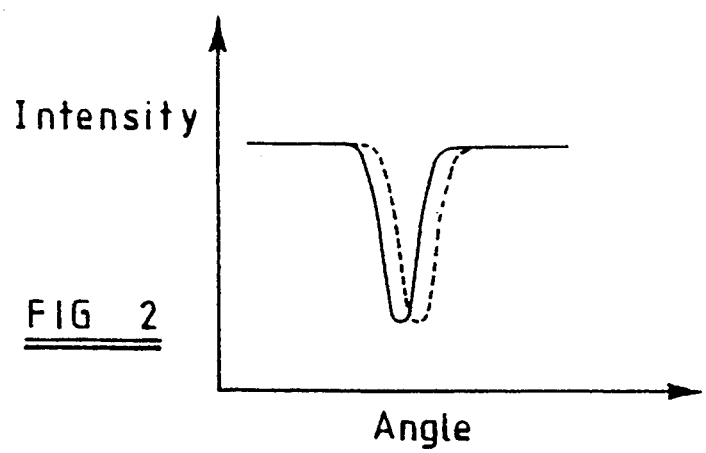
Figure 3:
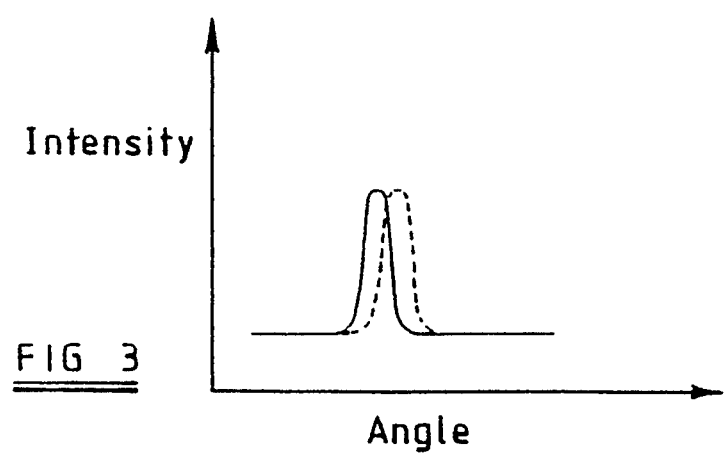

The invention will now be described in more detail, by way of illustration only, with reference to the accompanying drawings in which FIG. 1 is a schematic view (not to scale) of a biosensor according to the invention, FIG. 2 depicts the dependence of the intensity of the reflected light on the angle of incidence, and FIG. 3 depicts the dependence of the intensity of emitted fluorescence on the angle of incidence for a second embodiment.

Referring first to FIG. 1, a biosensor comprises a glass prism 1 coated over an area of its base with a first coating 2 of magnesium fluoride doped with copper fluoride and a second coating 3 of titanium dioxide. The prism 1 and first and second coatings 2, 3 together constitute a resonant optical structure, the first coating 2 acting as a spacer layer and the second coating 3 as a cavity layer. The first coating 2 has a thickness of approximately 1000 nm and the second coating 3 a thickness of approximately 100 nm.

In alternative embodiments, the first and second coatings 2, 3 comprise respectively
a) a metal and titanium dioxide, or
b) magnesium fluoride and doped titanium dioxide.

Immobilised on the surface of the second coating 3 is a layer 4 of immobilised biochemicals, which act as specific binding partner for the analyte under test.

The interface between the base of the prism 1 and the first coating 2 is irradiated by a fan-shaped beam of monochromatic light, internal reflection occurring and the intensity of the reflected radiation being measured by a detector (not shown) such as an array of photodiodes or charge coupled devices.

FIG. 2 shows the dependence of the reflected signal intensity as a function of the angle of incidence; at resonance, there is a sharp dip in the reflected intensity. The dotted line shows the corresponding result after binding of the immobilised chemicals 4 to their specific binding partner, ie the analyte to be determined. As can be seen, the position of resonance has shifted. This effect is used as a qualitative and/or quantitative indication of the presence of the analyte in the sample tested.

In alternative embodiments, the first and second coatings 2, 3 comprise respectively:
a) magnesium fluoride doped with a fluorophore; and titanium dioxide, or
b) undoped magnesium fluoride and titanium dioxide doped with a fluorophore.

In this case, the interface between the base of the prism 1 and the first coating 2 is irradiated with a beam of light which is scanned through a range of angles sequentially. Internal reflection occurs and the intensity of the emitted fluorescence is measured (in the direction of the arrow in FIG. 1).

FIG. 3 shows the dependence of the emitted fluorescence intensity as a function of the angle of incidence; at resonance, there is a sharp increase in the emitted fluorescence intensity. The dotted line shows the corresponding result after binding of the immobilised chemicals 4 to their specific binding partner (the analyte).

I claim:

1. A sensor including an optical structure comprising:
(a) a cavity layer (3) of dielectric material of refractive index $n_3$,
(b) a dielectric substrate (1) of refractive index $n_1$, and
(c) interposed between the cavity layer (3) and the substrate (1), a spacer layer (2) of refractive index $n_2$, $n_3$ and $n_1$ both being greater than $n_2$, the cavity layer (3) being of sufficient thickness to support at least one resonant mode, the arrangement being such that the optical structure may be illuminated by a beam of incident radiation, internal reflection occurring at the interface between the substrate (1) and the spacer layer (2), and the cavity layer (3) being coated with a layer of immobilized biochemicals (4), characterized in that the cavity layer (3) or the spacer layer (2) absorbs at the wavelength of the incident radiation.

2. A sensor as claimed in claim 1, wherein the spacer layer (2) comprises a metal or a dielectric material which either is strongly absorbing or which is doped with a strongly absorbing species.

3. A sensor as claimed in claim 1, wherein the cavity layer (3) comprises a dielectric material which either is strongly absorbing or which is doped with a strongly absorbing species.

4. A sensor as claimed in claim 1, wherein the cavity layer (3) is a thin-film of dielectric material.

5. A sensor as claimed in claim 4, wherein the spacer layer (2) has a thickness of from 200 nm to 2000 nm, and the cavity layer (3) has a thickness of from 10 to 200 nm.

6. A sensor as claimed in claim 5, wherein the cavity layer (3) has a thickness of 30 to 150 nm and comprises a material selected from zirconium dioxide, titanium dioxide, tantalum oxide and aluminum oxide, and the spacer layer (2) has a thickness of 500 to 1500 nm and comprises a material selected from magnesium fluoride, lithium fluoride and silicon dioxide, the choice of materials being such that the refractive index of the spacer layer (2) is less than that of the cavity layer (3), the spacer layer (2) or the cavity layer (3) containing an absorbing dopant.

7. A sensor as claimed in claim 1, wherein the spacer layer (2) or the cavity layer (3) contains a fluorophore.

8. A sensor as claimed in claim 1, further comprising means for irradiating the interface between the substrate (1) and the spacer layer (2) such that internal reflection occurs, and means for detecting radiation emitted from the optical structure.

9. A sensor as claimed in claim 8, Wherein the substrate-spacer layer interface is irradiated at a range of angles simultaneously.

10. A sensor as claimed in claim 8, wherein the substrate-spacer layer interface is irradiated at a range of angles sequentially.

11. A sensor as claimed in claim 1, wherein said dielectric substrate is coated with a multilayer structure comprising:
    (a) said cavity layer,
    (b) said spacer layer interposed between said cavity layer and said substrate, and
    (c) an additional thin layer of material which absorbs at the wavelength of the incident radiation.

* * * * *

UNITED STATES PATENT AND TRADEMARK OFFICE
CERTIFICATE OF CORRECTION

PATENT NO. : 5,434,663

DATED : July 18, 1995

INVENTOR(S) : COLIN H. MAULE

It is certified that error appears in the above-identified patent and that said Letters Patent is hereby corrected as shown below:

Column 4, line 1, "ill" should be --in--.

Column 7, line 10, "Wherein" should be --wherein--.

Signed and Sealed this

Twenty-first Day of November, 1995

Attest:

BRUCE LEHMAN

Attesting Officer

Commissioner of Patents and Trademarks